(12) United States Patent
Ghosh

(10) Patent No.: US 11,027,088 B2
(45) Date of Patent: Jun. 8, 2021

(54) NEONATAL INCUBATOR HUMIDIFIER SYSTEM

(71) Applicant: General Electric Company, Schenectady, NY (US)

(72) Inventor: Anirban Ghosh, Bengaluru (IN)

(73) Assignee: General Electric Company, Schenectady, NY (US)

( * ) Notice: Subject to any disclaimer, the term of this patent is extended or adjusted under 35 U.S.C. 154(b) by 169 days.

(21) Appl. No.: 16/240,359

(22) Filed: Jan. 4, 2019

(65) Prior Publication Data

US 2020/0215291 A1 Jul. 9, 2020

(51) Int. Cl.
| A61G 11/00 | (2006.01) |
| A61M 16/10 | (2006.01) |
| A61M 16/16 | (2006.01) |
| A61M 16/18 | (2006.01) |

(52) U.S. Cl.
CPC ........... *A61M 16/109* (2014.02); *A61G 11/00* (2013.01); *A61M 16/161* (2014.02); *A61M 16/183* (2013.01); *A61G 2203/46* (2013.01); *A61M 16/162* (2013.01); *A61M 2205/3368* (2013.01); *A61M 2240/00* (2013.01)

(58) Field of Classification Search
None
See application file for complete search history.

(56) References Cited

U.S. PATENT DOCUMENTS

| 5,381,836 | A  | 1/1995  | Braatz et al.    |
| 5,427,145 | A  | 6/1995  | Grabenkort       |
| 5,505,236 | A  | 4/1996  | Grabenkort et al.|
| 5,810,001 | A  | 9/1998  | Genga et al.     |
| 5,944,651 | A  | 8/1999  | Koch             |
| 6,125,893 | A  | 10/2000 | Braatz et al.    |
| 6,138,672 | A  | 10/2000 | Kankkunen        |
| 6,585,016 | B1 | 7/2003  | Falligant et al. |
| 6,745,800 | B1 | 6/2004  | Sansom           |
| 6,817,390 | B2 | 11/2004 | Falligant et al. |
| 6,878,133 | B2 | 4/2005  | Ahlmen et al.    |
| 6,929,041 | B2 | 8/2005  | Falligant et al. |
| 7,290,571 | B2 | 11/2007 | Bunke et al.     |
| 7,546,856 | B2 | 6/2009  | Chotenovsky      |
| 7,886,780 | B2 | 2/2011  | Falligant et al. |

(Continued)

FOREIGN PATENT DOCUMENTS

| DE | 19954097 | 5/2000  |
| EP | 2645070  | 10/2013 |

(Continued)

*Primary Examiner* — Christine M Matthews
(74) *Attorney, Agent, or Firm* — Andrus Intellectual Property Law, LLP

(57) ABSTRACT

A humidifier system for humidifying a microenvironment in a neonatal incubator includes a reservoir configured to hold water to be evaporated for humidifying the microenvironment. A chamber divider defines a heating chamber within the reservoir, and a movable heating element is positioned at a surface level of the water inside the heating chamber so as to heat the water at the surface level inside the heating chamber. The heating element is configured such that it is moved downward within the heating chamber so as to maintain the heating element at the surface level of the water as an amount of water in the reservoir decreases.

19 Claims, 4 Drawing Sheets

(56) References Cited

U.S. PATENT DOCUMENTS

| | | |
|---|---|---|
| 8,522,839 B2 | 9/2013 | Freed et al. |
| 8,783,248 B2 | 7/2014 | Heinonen et al. |
| 8,867,031 B2 | 10/2014 | Jones et al. |
| D741,879 S | 10/2015 | Chapman et al. |
| 9,217,658 B2 | 12/2015 | Kuehl et al. |
| 2002/0069876 A1 | 6/2002 | Loser et al. |
| 2003/0197003 A1 | 10/2003 | Kneuer |
| 2007/0114292 A1 | 5/2007 | Breed et al. |
| 2008/0105257 A1* | 5/2008 | Klasek .............. A61M 16/0633 128/203.27 |
| 2009/0149927 A1* | 6/2009 | Kneuer ................. G05D 23/00 607/96 |
| 2009/0177257 A1 | 7/2009 | Khodak et al. |
| 2012/0318263 A1 | 12/2012 | Jones et al. |
| 2012/0318264 A1 | 12/2012 | Jones et al. |
| 2013/0126464 A1 | 5/2013 | Manzke et al. |
| 2015/0182722 A1 | 7/2015 | Lesch et al. |
| 2015/0306339 A1 | 10/2015 | Danielsen |

FOREIGN PATENT DOCUMENTS

| | | |
|---|---|---|
| FR | 2570609 | 3/1986 |
| WO | 2000027458 | 5/2000 |
| WO | 2005056093 | 6/2005 |
| WO | 2007006348 | 1/2007 |
| WO | 2008151667 | 12/2008 |

\* cited by examiner

NEONATAL INCUBATOR HUMIDIFIER SYSTEM

BACKGROUND

The present disclosure generally regards incubator systems providing a microenvironment for a neonate, and more specifically to a neonatal incubator having a humidifier system configured to reduce sound levels generated due to heating the evaporant.

Neonatal incubators create a microenvironment that is thermally neutral where a neonate can develop. These incubators typically include a humidifier and associated control system that controls the humidity in the neonatal microenvironment. The humidifier comprises a device that evaporates an evaporant, such as distilled water, to increase relative humidity of air within the neonatal microenvironment. Such humidifiers typically have an evaporant source in the form of a reservoir that holds water to be dispersed into the microenvironment within the incubator. For example, the humidifier may be a steam humidifier or vaporizer in which the water is heated to cause evaporation. The humidifier is typically controllable such that the amount of water, or water vapor, added to the microenvironment is adjustable in order to control the humidity to a desired value.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a humidifier system for humidifying a microenvironment in a neonatal incubator includes a reservoir configured to hold water to be evaporated for humidifying the microenvironment. A chamber divider defines a heating chamber within the reservoir, and a movable heating element is positioned at a surface level of the water inside the heating chamber so as to heat the water at the surface level inside the heating chamber. The heating element is configured such that it is moved downward within the heating chamber so as to maintain the heating element at the surface level of the water as an amount of water in the reservoir decreases.

One embodiment of a neonatal incubator comprises a bed configured to support a neonate and a hood above the bed configured to encapsulate a microenvironment around the neonate. A humidifier system is configured to control humidity of the microenvironment, the humidifier system having a reservoir configured to hold water to be evaporated for humidifying the microenvironment, and a heating chamber divider defining a heating chamber within the reservoir. A movable heating element is positioned at a surface level of the water inside the heating chamber so as to heat the water at the surface level inside the heating chamber. The heating element is moved downward within the heating chamber so as to maintain the heating element at the surface level of the water as an amount of water in the reservoir decreases.

Various other features, objects, and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

Figure 1:
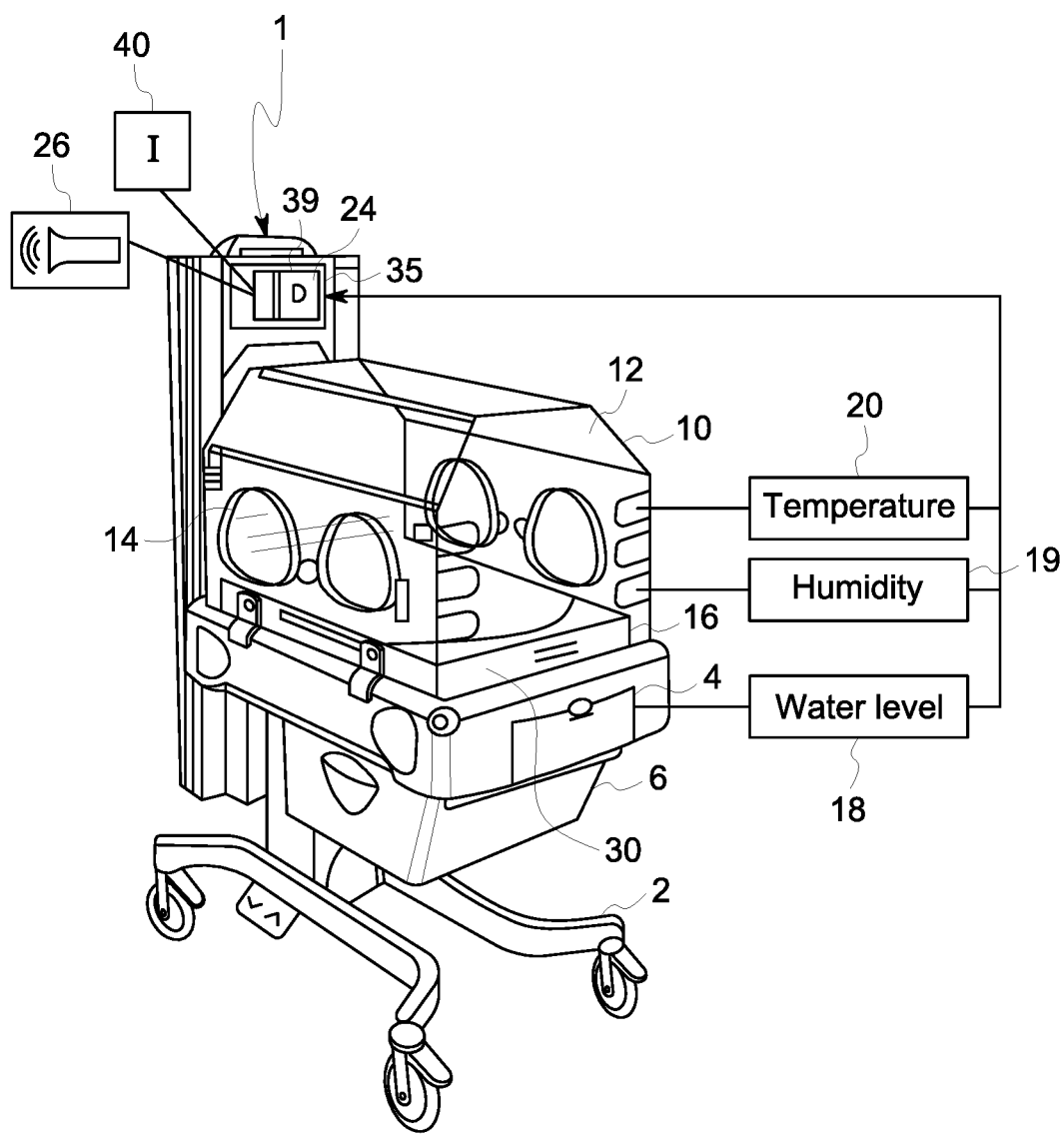
FIG. 1 is a perspective view of an exemplary incubator containing a humidifier system, including a schematic diagram depicting relevant sensing and control elements for the humidifier system.

Through extensive experimentation and research in the field of neonatal incubators, the present inventor has recognized that present incubator systems using heated water generate too much noise. The high noise levels generated by current humidifier systems can negatively affect an infant housed in the incubator. Neonates are known to be detrimentally affected by increased sound levels inside the microenvironment of an incubator. The inventor has recognized that the sound level in an incubator can be significantly reduced by changing existing humidifier systems to reduce or eliminate bubbling, or boiling, of the water. Present incubator systems heat the water at the bottom of the reservoir, causing the water to boil up to the top. This boiling generates a bubbling sound, which sometimes can be quite loud and the greatest source of noise generation in the incubator.

The disclosed system significantly reduces or eliminates the sound caused by the boiling water by only heating the water surface and not heating water in the lower portion of the reservoir, thereby eliminating the bubbling sound. The disclosed humidifier system implements a movable heating element that is maintained at a surface level of the water. In one embodiment, the heating element is contained in a heating chamber within the reservoir and is positioned to just heat the water at the surface level inside the heating chamber. The heating element is configured so that it can be maintained at or near the water surface such that only water near the water surface boils and water located in a lower portion of the heating chamber does not boil.

The heating element is thus shorter, or thinner, compared to heating elements implemented in prior art systems where the heating was concentrated in a lower portion of the reservoir, creating the boiling action. Existing humidifier systems include one or more heating rods that extend to the bottom of the reservoir, wherein the heating element occupies at least the bottom third of the heating rod, or more. One example of an existing heating element includes a stainless steel rod that extends down into the reservoir, wherein one or more heating elements transmit heat to the water from the bottom portion of the rod, such as the bottom third or bottom half of the rod length. The water surrounding the bottom portion of the rod is heated to a boiling point, causing bubbles to rise from the bottom to the top of the water reservoir. The noise from the boiling action echoes within the reservoir and surrounding chambers, thus making the boiling sound pronounced for the infant. Moreover, such existing systems heat large volumes of water in order to cause evaporation, which is inefficient.

In the disclosed system, the shorter heating element is moved downward as the amount of water in the reservoir decreases such that the heating element is always maintained at the surface level of the water. The heating element may be configured and maintained at the surface level by various means, examples of which are described herein. In one embodiment, the heating element is configured such that it floats on the water surface. In other embodiments, a mechanism, such as a spring or a lead screw, works in combination with the buoyancy force of the water in order to maintain the heating element at the surface level.

FIG. 1 depicts one embodiment of an incubator system 1 having a bed 16 supported by a base 2. In the depicted embodiment, the base 2 is on wheels to facilitate transit of an infant in the incubator system 1. The depicted incubator system 1 has a hood 10 defining a chamber 12 creating a microenvironment for housing a neonate. The hood 10 comprises a transparent housing extending above the bed 16. In the example, the hood 10 includes a plurality of portholes 14 through which a healthcare provider may access the one or more infants within the chamber 12. The depicted hood 109 comprises a single structure movable as a unit. In other implementations, sidewalls of the hoods 10 may remain about the bed 16 forming a crib, wherein the top-most portion is separable and/or removable from the sidewalls to access the one or more infants supported in the microenvironment.

The bed 16 may further include heating component(s) 30 used to control the temperature within the microenvironment of the chamber 12. For example, the chamber heater 30 may be a radiant heating or warming device that heats the air within the chamber 12 to a predefined temperature or within a predefined temperature range. In another embodiment, the heater 30 may comprise a convective or conductive heating device or any other type of controllable heating or warming device.

The incubator system 1 further includes a humidifier system 4 controllable to adjust the relative humidity within the chamber 12. The humidifier comprises a device that evaporates water, such as distilled water 7, to increase relative humidity of air within the neonatal microenvironment. The humidifier system 4 has a water reservoir 6 containing evaporant, such as distilled water, utilized for humidification of the chamber 12. The water reservoir 6 is a tank or other vessel capable of holding the evaporant. Although the water reservoir 6 in the illustrated embodiment is located below the bed 16, in other embodiments the water reservoir 6 may be provided at other locations. In one embodiment, the water reservoir 6 is removable from the incubator system 1 for draining and/or cleaning purposes. In other embodiments, the reservoir 6 may remain attached to the incubator system 1 and may provide other access for the purpose of draining the evaporant from the reservoir 6 and/or cleaning the reservoir 6. A water level sensor 18 may sense the water level within the reservoir 6 and generate a water level indicator value, such as to modify a clinician that water needs to be added to the reservoir 6. Additionally, one or more sensors may be provided to sense temperature and humidity within the microenvironment of the chamber 12, such as humidity sensor 19 and temperature sensor 20.

The sensors 18, 19, 20 provide the sensed information to the control system 35, which controls various elements within the incubator system 1. The control system 35 includes a computing system having a processor and a memory capable of storing software for providing various control functions, including for controlling the humidifier in order to maintain a particular humidity level within the chamber 12. In the depicted embodiment, the incubator system 1 further includes a user interface 39 comprising a display 24, a speaker 26, and an input 40. Such user interface 39 elements are used to provide information to a clinician regarding the status and condition of the incubator system 1, as well as to receive control inputs from a clinician to control various aspects of the incubator system 1, including to control the environment within the chamber 12. The display 24 includes any visual output device, examples of which include a digital display screen, monitor, or the like (which may also be a touchscreen) that presents visible notifications or messages to a clinician.

The display 24 may include a monitor independent of the bed portion of the incubator incorporated into some portion. In another implementation, the display 24 may comprise a screen of a portable computing or electronic device, such as a smartphone or tablet computer. Likewise, the speaker 26 may be any audio output device and may be incorporated into the bed portion of the incubator system, or may be included in a separate device, such as in the personal computing device described above. Likewise, the input 40 may be any device that facilitates user input of information, such as commands, selection, data, or settings for the incubator system 1. In one implementation, the input 40 may include a keyboard, touchpad, touchscreen, mouse, or microphone with speech recognition software, or the like. Thus, the user interface 39 may be configured to allow a user, such as a clinician, to set a humidity level for the microenvironment, and the control system 35 controls operation of the humidifier 4 to maintain the humidity at the selected humidity level. To provide just one example, the user interface may be configured to allow a clinician to set a relative humidity percentage for the microenvironment, such as a humidity level between 30% and 95%. The control system 35 then generates control instructions to control current to one or more heating elements within the humidifier system 4 in order to control the amount of water evaporated from the reservoir, and thereby to control the humidity level in the microenvironment within the chamber 12.

Figure 2:
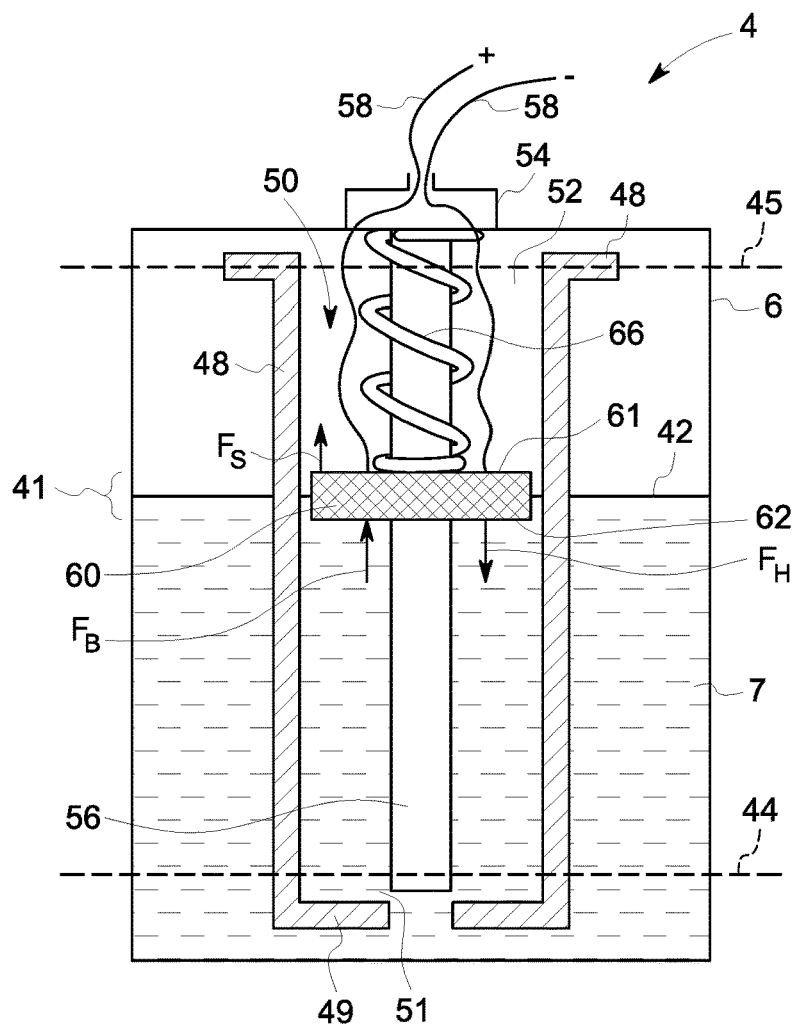
FIG. 2 is a schematic depiction of a reservoir in an incubator system having an exemplary heating element and configuration according to one embodiment of the present disclosure.

FIG. 2 represents one embodiment of a humidifier reservoir 6 and heating element configuration. A small heating element 60 is suspended at a surface level 41 of the water 7 inside the reservoir 6. As the amount of water 7 in the reservoir 6 decreases due to its evaporation, the heating element 60 moves downward such that it is maintained at the surface level 41 of the water 7. The surface level 41 of the water 7 is aligned with the water surface 42, such that a bottom side 62 of the heating element 60 is maintained at or below the water surface 42 and a top side 61 of the heating element 60 is maintained above the water surface 42.

In the depicted embodiment, a heating chamber 50 is defined within the reservoir 6, which reduces the amount of water exposed to the heating element 60 and thus provides more efficient evaporation. The heating chamber 50 is defined by a chamber divider 48, which partitions a space within which the heating element 60 moves as the water 7 in the reservoir 6 is depleted and the surface level 41 moves down. In one embodiment, the chamber divider 48 is comprised of a thermally resistant material, such as plastic, in order to maintain the heat from the heating element 60 within the water in the heating chamber 50 as much as possible. The heating chamber 50 may be defined at any location within the reservoir 6, which may be within a center portion or an edge portion of the reservoir 6.

The heating element 60 moves up and down within the chamber 50 to accommodate a range of surface levels 41, from a highest level in line with the maximum fill level 45 to a lowest level in line with the minimum fill level 44. In one embodiment, the chamber divider 48 has a bottom edge 49 configured to stop the heating element 60 when the surface level 41 has gotten too low, such as the minimum fill level 44. In one embodiment, the humidifier system 4 is configured to shut off when the heating element 60 reaches the bottom edge 49 of the chamber divider 48. In other embodiments, the humidifier system 4 may be configured to shut off when the surface level 41 reaches some predetermined point before the heating element 60 reaches the bottom edge 49, such that the heating element 60 never reaches the bottom edge 9 when the humidifier system 4 is operating.

Figure 3:
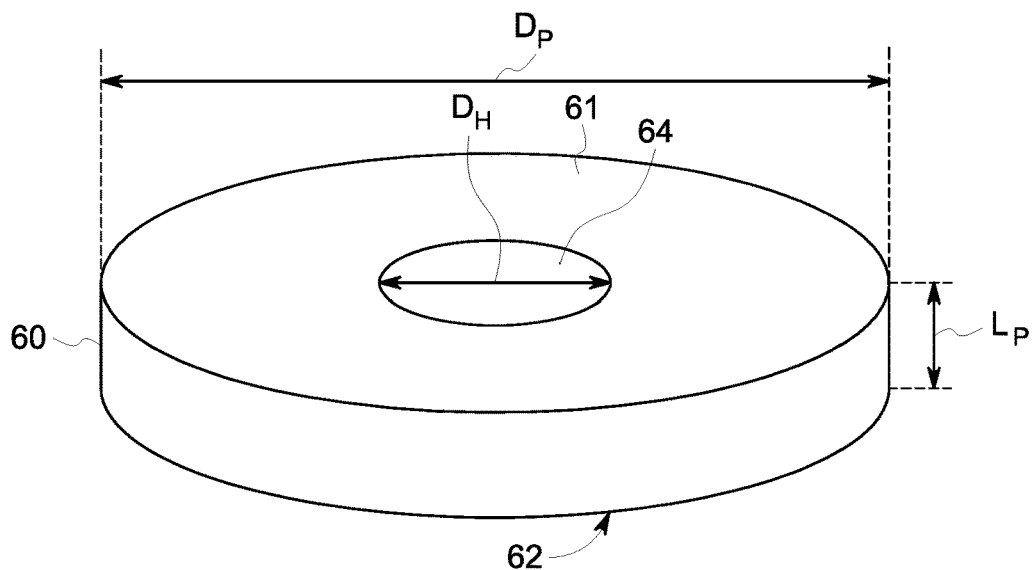
FIG. 3 depicts one embodiment of a puck-shaped heating element according to one embodiment of the present disclosure.

In one embodiment, the heating element 60 is moved up and down along a guide 56, such as a rod. The guide 56 may be suspended from a top element 54 and span from a top portion 51 of the chamber 50 to a bottom portion 52 of the chamber 50. The guide 56 spans at least a distance to guide the heating element 60 from a maximum fill level 45, where a maximum amount of water 7 is in the reservoir 6, and a minimum fill level 44, where a minimum amount of water 7 is contained in the reservoir 6. In one embodiment, the heating element 60 is configured with a hole 64 (FIG. 3) that allows the heating element 60 to move up and down with respect to the guide 56. The guide 56 may be configured such that it prevents lateral movement of the heating element 60 but allows easy vertical movement. For example, the heating element 60 may have a hole 64 with a diameter $D_H$ that is only slightly larger than a diameter of the guide 56. Thereby, the heating element 60 is maintained in a centered position within the chamber 50 and prevented from impacting the chamber divider 48, which could cause additional noise and also make the heating less efficient where the portion of the heating element 60 contacting the chamber divider 48 is not in contact with the water 7. However, in other embodiments no guide is provided (e.g. FIG. 5).

The heating element 60 may be any of various shapes capable of being suspended at the surface level 41. As exemplified in FIG. 3, the heating element 60 may be puck-shaped, or cylindrical, having a top side 61 that is above the water surface 42 and the bottom side 62 that is at or slightly below the water surface 42. The puck-shaped heating element 60 has a length $L_p$ between the top side 61 and the bottom side 62. The length $L_p$ may vary; however, the heating element 60 is generally short such that the heating element 60 does not extend deep into the water 70 so as not to cause the bubbling effect described above. In one exemplary embodiment, the length $L_p$ of the heating element 60 may be 20 mm or less. In another embodiment, the length $L_p$ of the heating element 60 may be 15 mm or less, or may be 12 mm or less. Minimizing the length $L_p$ is desirable to heat only the water surface 42. In the depicted embodiment, the heating element 60 has a hole 64 in the center, wherein the hole has a diameter $D_H$. In other embodiments, the heating element 60 may not have any hole, and thus may not be configured to slide along a guide 56. The puck-shaped heating element 60 has a diameter $D_p$. The diameter $D_p$ may be any size, depending on the operational demand for which the humidifier system 4 is configured. In one exemplary embodiment, the diameter $D_p$ of the puck-shaped heating element 60 is 25 mm or less.

In other embodiments, the heating element 60 may be shaped differently. For instance, the heating element may be spherical, or may otherwise have a curved bottom side 62 and/or top side 61. In other embodiments, the heating element may be cone-shaped having a point that extends below the water surface 42. In still other embodiments, the heating element 60 may be rectangular or a cube.

The chamber 50 is sized to accommodate the heating element 60. Thus, where the heating element 60 is puck-shaped, the chamber is cylindrical. In an embodiment where the heating element 60 is a square or a rectangle, the heating chamber 50 may have the same shape. The dimensions of the heating chamber 50 may generally follow those of the heating element 60, being slightly larger so as to permit the heating element 60 to move freely up and down within the chamber 50 and allowing a small amount of water to fill a gap between the heating element 60 and the chamber divider 48. To provide just one example, a distance of at least 1.5 mm may be maintained between the surrounding edge of the heating element 60 and the chamber divider 48.

The heating element may be maintained at the surface level 41 of the water 7 by various means or mechanisms. In some embodiments where the relative density of the heating element is greater than that of water, the heating element 60 will sink without some mechanism providing an upward force on the heating element 60. Referring again to FIG. 2, the weight of the heater $F_H$ must be counteracted by an upward force acting on the heating element 60. The water 7 provides a buoyancy force $F_B$ that pushes up on the heating element 60. In some embodiments where the relative density of the heating element is lower than that of water, the buoyancy force $F_B$ will be enough to maintain the heater at the surface level 41. In other embodiments, like that depicted in FIGS. 2 and 3, an additional mechanism is needed to compensate for the difference between the downward-acting weight of the heater $F_H$ and the upward-acting buoyancy force $F_B$. In FIG. 2, a tension spring 66 connects between the top of the reservoir 6 and/or the top element 54 and the heating element 60 in order to provide an upward-acting spring force $F_S$ that, in conjunction with the buoyancy force $F_B$, counteracts the weight $F_H$ of the heating element 60. Accordingly, a spring 66 is chosen that provides a spring force $F_S$ calibrated to compensate for the difference between the heater weight $F_H$ and the buoyancy force $F_B$ so that the heating element 60 is maintained at the surface level 41. Moreover, the tension spring 66 is configured such that it provides a constant spring force $F_S$ on the heating element across a range of water levels 42 between the maximum fill level 45 and the minimum fill level 44.

In another embodiment, the additional vertical force needed to counteract the heater weight $F_H$ may be provided by threads 57 on the guide 56. In other words, the guide 56 may be a lead screw with threads 57 provided at angles calibrated to provide an upward force equal to the difference between the heater weight $F_H$ and the buoyancy force $F_B$. The thread angles of the threads 57 may be steeper (a higher angle as measured from horizontal) to provide a lesser upward force or less steep to provide a greater upward force. In certain embodiments, the interior side of the hole 64 in the heating element 60 may be threaded to correspond to the thread angle of the threads 57 on the guide 56 such that the heating element 60 remains level and parallel with the water surface 42. Accordingly, the heating element 60 rotates downward on the lead screw guide 56 as the amount of water 7 in the reservoir 6 decreases.

Figure 5:
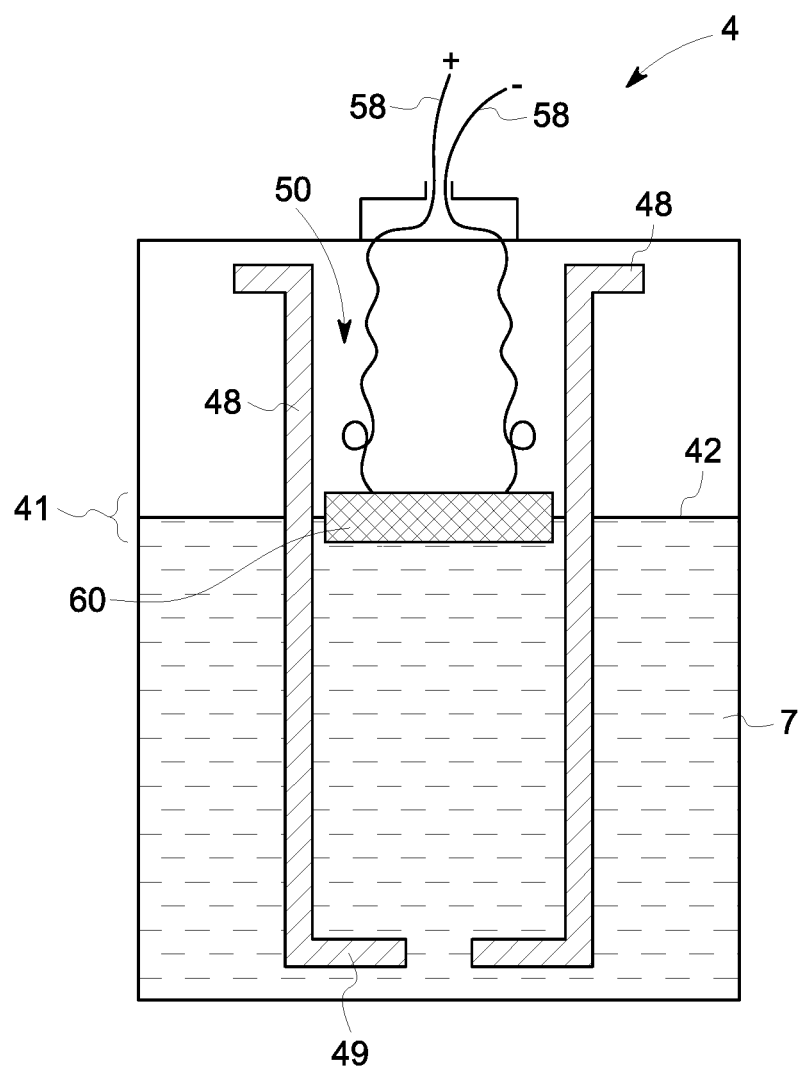
FIG. 5 is a schematic depiction of a reservoir in an incubator system comprising yet another exemplary heating element and configuration.

FIG. 5 depicts another embodiment where the heating element 60 has a lower relative density than water such that the heater weight $F_H$ is less than the buoyancy force $F_B$. For example, the heating element 60 may be a silicon heater where a heating coil or wire is encased in silicon, such as a silicon disk to form a puck-shaped heating element 60 similar to that depicted at FIG. 3. In various embodiments, the buoyant heating element 60 may float freely within the heating chamber 50, or may be held in place by a guide 56. Where no guide is used, the heating element 60 may be solid, i.e., without the hole 64 shown in FIG. 3. Where a guide 56 is present, the buoyant heating element 60 is provided with a hole 64 therethrough such that the heating element 60 floats up and down with respect to the guide 56.

Power is provided to the heating element 60. In the depicted embodiments, wires 58 extend from the heating element 60 connecting to the heating circuit therein. The wires 58 are provided with sufficient slack such that the heating element 60 can move freely within the range of surface levels 41 between the maximum fill level 45 and the minimum fill level 44. In the figures, the wires 58 are shown as having slack contained within the heating chamber 50. In other embodiments, the wires 58 may travel within the guide 56, where one is provided, and the guide 56 may have one or more openings, or slots, running the length of the guide 56 (or at least between the maximum fill level 45 and minimum fill level 44) such that the wires connect with the heating circuit within the heating element 60. In the spring embodiment, the wires may travel generally parallel with the spring 66.

Figure 4:
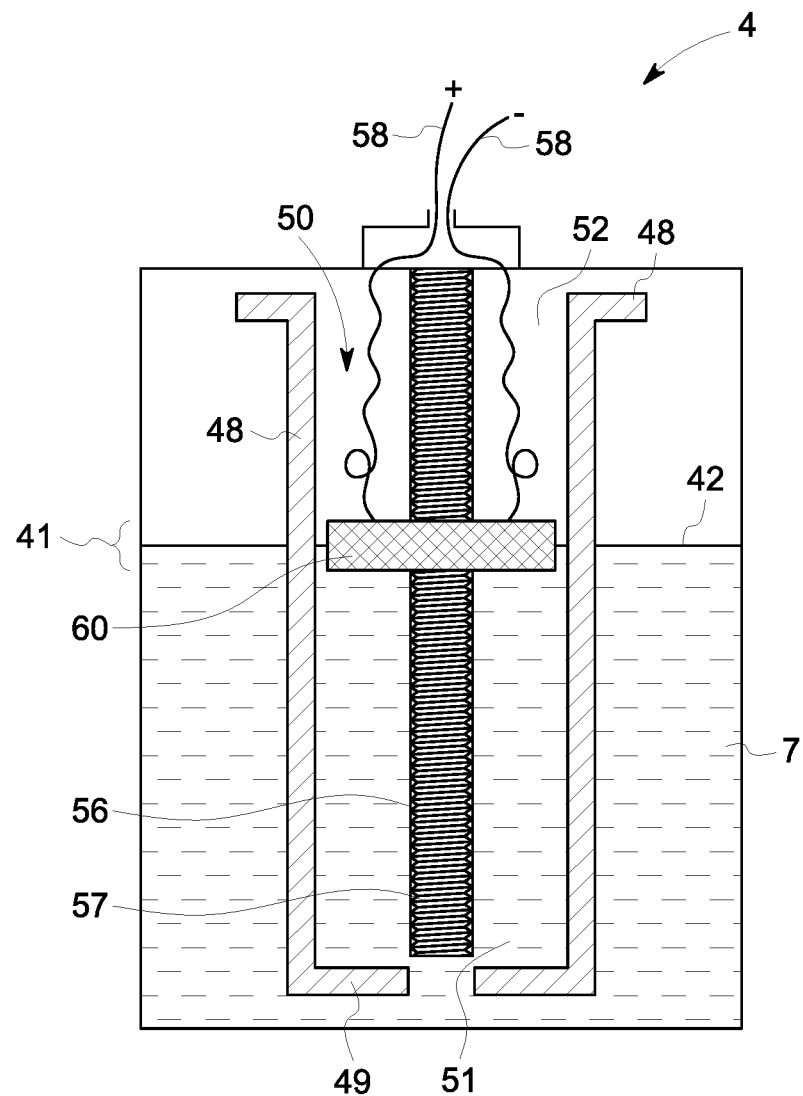
FIG. 4 is a schematic depiction of a reservoir in an incubator system comprising another embodiment of a heating element and configuration.

In still other embodiments, the entire surface of the guide 56 is conductive and the interior surface of the hole 64 in the heating element 60 is configured to remain in contact with the guide 56 as the heating element 60 moves up and down within the heating chamber 50. In another example, contact strips or rings may be provided running the length of the guide 56. In the spring embodiment depicted at FIG. 2, for instance, positive and negative terminal strips may run the length of the guide 56, and the heating element 60 and guide 56 may be configured such that the orientation of the heating element 60 remains fixed with respect to the guide such that terminals on the heating element 60 remain in contact with the terminal strips on the guide 56 as the heating element 60 moves up and down within the heating chamber 50. In the lead screw embodiment depicted at FIG. 4, for example, contact strips may twist around the guide 56 parallel with the threads 57 such that corresponding terminals on the heating element 60 remain in contact with the terminal strips.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. A humidifier system for humidifying a microenvironment in a neonatal incubator, the humidifier system comprising:
    a reservoir configured to hold water to be evaporated for humidifying the microenvironment;
    a chamber divider defining a heating chamber within the reservoir;
    a movable heating element positioned at a surface level of the water inside the heating chamber so as to heat the water at surface level inside the heating chamber;
    wherein the heating element is moved downward within the heating chamber as an amount of water in the reservoir decreases so as to maintain the heating element at the surface level of the water; and
    wherein the heating element has a hole that accommodates a guide, and wherein the heating element slides down the guide as it moves downward within the heating chamber.

2. The humidifier system of claim 1, wherein the heating element is configured and positioned such that only water near the surface level boils and water located in a lower portion of the heating chamber does not boil.

3. The humidifier system of claim 1, wherein the heating element is puck-shaped, wherein a top side of the puck-shaped heating element is maintained above a water surface and bottom side of the puck-shaped heating element is maintained at or below the water surface.

4. The humidifier system of claim 3, wherein the heating chamber is cylindrical.

5. The humidifier system of claim 1, wherein the heating element is maintained at the surface level of the water by a tension spring exerting a spring force calibrated based on a weight of the heating element and a buoyancy force of the water on the heating element to maintain the heating element at the surface level as the amount of water in the reservoir decreases.

6. A humidifier system for humidifying a microenvironment in a neonatal incubator, the humidifier system comprising:
    a reservoir configured to hold water to be evaporated for humidifying the microenvironment;
    a chamber divider defining a heating chamber within the reservoir;
    a movable heating element positioned at a surface level of the water inside the heating chamber so as to heat the water at surface level inside the heating chamber;
    wherein the heating element is moved downward within the heating chamber as an amount of water in the reservoir decreases so as to maintain the heating element at the surface level of the water; and
    wherein the heating element is maintained at the surface level of the water by a tension spring exerting a spring force calibrated based on a weight of the heating element and a buoyancy force of the water on the heating element to maintain the heating element at the surface level as the amount of water in the reservoir decreases.

7. The humidifier system of claim 1, wherein the heating element is configured to float on the water inside the heating chamber.

8. The humidifier system of claim 7, wherein the heating element is a silicon puck, wherein a weight of the heating element is less than a buoyancy force of the water acting on the heating element.

9. The humidifier system of claim 1, wherein the guide is a leadscrew with thread angles calibrated based on a weight of the heating element and a buoyancy force of the water on the heating element to maintain the heating element at the surface level as the amount of water in the reservoir decreases.

10. A neonatal incubator comprising:
    a bed configured to support a neonate;
    a hood above the bed configured to encapsulate a microenvironment around the neonate;
    a humidifier system configured to control humidity of the microenvironment, the humidifier system having:
        a reservoir configured to hold water to be evaporated for humidifying the microenvironment;

a heating chamber divider defining a heating chamber within the reservoir;

a movable heating element positioned at a surface level of the water inside the heating chamber so as to heat the water at surface level inside the heating chamber;

wherein the heating element is moved downward within the heating chamber as an amount of water in the reservoir decreases so as to maintain the heating element at the surface level of the water; and wherein the heating element has a hole that accommodates a guide, and wherein the heating element slides down the guide as it moves downward within the heating chamber.

11. The neonatal incubator of claim 10, wherein the heating element is configured and positioned such that only water near the surface level boils and water located in a lower portion of the heating chamber does not boil.

12. The neonatal incubator of claim 10, wherein the heating element is puck-shaped, wherein a top side of the puck-shaped heating element is maintained above a water surface and bottom side of the puck-shaped heating element is maintained at or below the water surface.

13. The neonatal incubator of claim 12, wherein the heating chamber is cylindrical.

14. The neonatal incubator of claim 10, wherein the heating element is maintained at the surface level of the water by a tension spring exerting a spring force calibrated based on a weight of the heating element and a buoyancy force of the water on the heating element to maintain the heating element at the surface level as the amount of water in the reservoir decreases.

15. The neonatal incubator of claim 14, wherein the tension spring is configured to provide a constant spring force on the heating element across a range of surface levels from a maximum fill level to a minimum fill level.

16. The neonatal incubator of claim 10, wherein the heating element is configured to float on the water inside the heating chamber.

17. The neonatal incubator of claim 16, wherein the heating element is a silicon puck, wherein a weight of the heating element is less than a buoyancy force of the water acting on the heating element.

18. The neonatal incubator of claim 10, wherein the guide is a leadscrew with thread angles calibrated based on a weight of the heating element and a buoyancy force of the water on the heating element to maintain the heating element at the surface level as the amount of water in the reservoir decreases.

19. The humidifier system of claim 6, wherein the tension spring is configured to provide a constant spring force on the heating element across a range of surface levels from a maximum fill level to a minimum fill level.

* * * * *